United States Patent [19]

Field et al.

[11] 4,067,912
[45] Jan. 10, 1978

[54] PRODUCTION OF PHENOLS

[75] Inventors: Peter Graham Spencer Field, Poulton-cum-Spital; Ronald Bennett, Chester, both of England

[73] Assignee: Burmah Oil Trading Limited, Cheshire, England

[21] Appl. No.: 594,681

[22] Filed: July 10, 1975

[30] Foreign Application Priority Data

July 19, 1975 United Kingdom ............... 32153/75

[51] Int. Cl.$^2$ ....................... C07C 37/08; C07C 39/06
[52] U.S. Cl. .............................. 260/621 C; 260/624 R
[58] Field of Search ........ 260/621 C, 624 R, 624 RR, 260/619 R, 624

[56] References Cited

U.S. PATENT DOCUMENTS

| 2,661,375 | 12/1953 | Conner | 260/601 |
| 2,889,368 | 6/1959 | Hiratsuka et al. | 260/593 |
| 2,993,074 | 7/1961 | Shepard | 260/593 |
| 3,928,477 | 12/1975 | Field | 260/621 |

Primary Examiner—James O. Thomas, Jr.
Assistant Examiner—W. B. Lone
Attorney, Agent, or Firm—Browdy and Neimark

[57] ABSTRACT

Phenols are prepared by decomposing aromatic hydroperoxides in the presence of a catalyst comprising a compound containing a heterocyclic ring of the structure

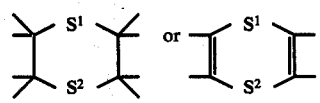

wherein $S^1$ and $S^2$ each independently represents a sulphur atom or a sulphoxide or sulphone group.

21 Claims, No Drawings

PRODUCTION OF PHENOLS

This invention relates to a process for the production of phenols by decomposing aromatic organic hydroperoxides.

Phenol is commonly produced on a large scale by decomposing cumene hydroperoxide in the presence of an acid catalyst, for example, sulphuric acid or perchloric acid. The mechanism of the reaction, when catalyzed by sulphuric acid is believed to be as follows:

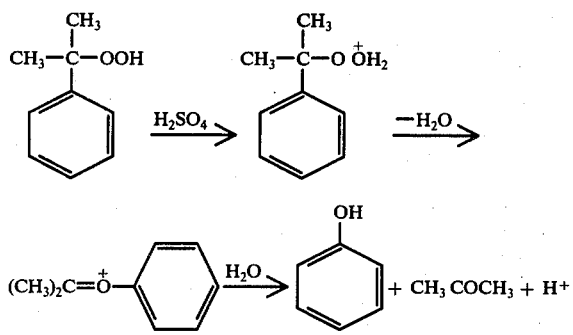

II

Thus the cumene hydroperoxide is protonated to form an intermediate I which loses water and rearranges to form the intermediate II which reacts with water to yield phenol and acetone.

The hydroperoxide is normally formed by autoxidation of cumene (isopropylbenzene) and the latter can be formed by alkylation of benzene with propylene. Other tertiary aralkyl hydroperoxides can be decomposed in the presence of acid catalysts to yield substituted phenols. Thus, for example, para-cresol has been prepared by decomposing para-cymene hydroperoxide.

It has not hitherto been considered commercially practicable to effect the decomposition of hydroperoxides other than tertiary aralkyl hydroperoxides, since firstly the yields of phenols produced have been commercially unattractive and secondly, as in the case of tertiary hydroperoxides, undesirable quantities of high molecular weight by-products are produced when conventional acid catalysts are used.

Furthermore, while the use of conventional acid catalysts to catalyze the decomposition of tertiary aralkyl hydroperoxides to phenols and ketones has led to reported yields of up to about 90 wt % phenol and 80 wt % ketone, based on the hydroperoxide, it is generally found that when using such catalysts, a proportion of the hydroperoxide starting material tends to be converted into very undesirable contaminants by means of competing side reactions. Thus, it is common for the product obtained when cumene hydroperoxide is decomposed in the presence of conventional acid catalysts to contain a proportion of high molecular weight resinous materials and other high boiling materials produced in the reaction. The need to remove these materials can necessitate further process stages and can complicate the recovery of the phenol.

A further disadvantage of the use of conventional acid catalysts is that it is generally necessary to construct the plant used to carry out the decomposition from corrosion-resistant materials and this can result in high capital costs.

Furthermore, it is generally necessary to remove or neutralize the acid catalyst before the decomposition products are processed to recover phenol.

We have now discovered a novel catalyst for this purpose the use of which raises the yields of phenols or substituted phenols from secondary aralkyl hydroperoxides to a level which makes this route to the phenols or substituted phenols commercially attractive. Use of this catalyst also reduces the quantity of high molecular weight by-products formed for both secondary and tertiary hydroperoxides. Also, since the catalyst is not strongly acidic in nature, the vessels used for carrying out the decomposition need not be constructed of such corrosion-resistant materials as are required when conventional acid catalysts are used and there is also no need to remove the catalyst before the phenols are recovered, although this may be effected if desired.

According to the present invention, there is provided a process for producing a phenol or a substituted phenol by decomposing an aromatic organic hydroperoxide, which process comprises effecting the decomposition in the presence of a catalyst comprising a compound containing a heterocyclic ring of the structure

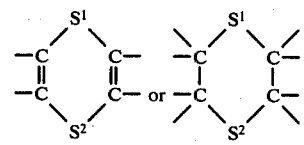

wherein $S^1$ and $S^2$ each independently represents a sulphur atom or a sulphoxide or sulphone group.

The structure of the compound used as catalyst in the process of the invention may, for example, be represented by the formula

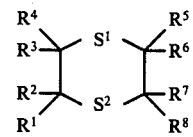

wherein $R^1$, $R^4$, $R^5$ and $R^8$ each independently represents a hydrogen atom or a substituted or unsubstituted hydrocarbyl group, $R^2$ and $R^3$ each independently represents a hydrogen atom, a substituted or unsubstituted hydrocarbyl group, or together represent an additional bond linking the carbon atoms to which they are attached, $R^6$ and $R^7$ each independently represents a hydrogen atom, a substituted or unsubstituted hydrocarbyl group, or together represent an additional bond linking the carbon atoms to which they are attached, and $S^1$ and $S^2$ are as defined above.

Examples of such compounds are those having the formulae

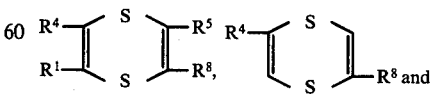

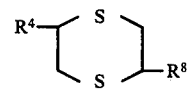

and the corresponding sulphones and sulphoxides.

Generally, however, compounds containing the unsaturated dithiin ring

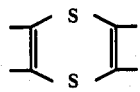

are preferred on account of their more pronounced catalytic activity.

Examples of unsubstituted hydrocarbyl groups represented by $R^1$, $R^2$, $R^3$, $R^4$, $R^5$, $R^6$, $R^7$ and $R^8$ are straight and branched chain alkyl groups, for example, such groups containing from 1 to 8 carbon atoms, such as methyl, ethyl, n-propyl, iso-propyl, butyl, amyl, hexyl, heptyl, octyl and preferably straight and branched chain lower alkyl groups containing from 1 to 4 carbon atoms. Further examples include aryl groups (including alkaryl groups) and aralkyl groups. Preferably the aryl and aralkyl groups contain from 6 to 24 carbon atoms, most preferably 6 to 14 carbon atoms and may, for example, comprise a phenyl or naphthyl group.

Examples of substituents on the hydrocarbyl groups represented by $R^1$ to $R^8$ include halogen atoms and alkoxy and nitro groups.

Preferably, the catalyst comprises a compound of the formula

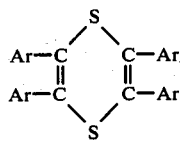

wherein Ar represents an aryl group, for example a phenyl group, an example of such a compound being tetraphenyl dithiin (2,3,5,6-tetraphenyl-1,4-thiadiene) having the formula

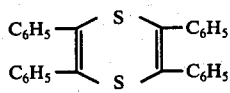

Further examples of representative compounds are:
1. 2,5-diphenyl-1,4-dithiin

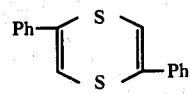

2. 2,5-di-t-butyl-1,4-dithiin

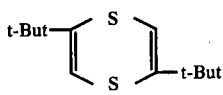

3. 2,5-dioctyl-1,4-dithiane

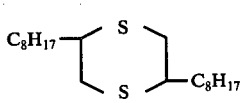

4. 2,5-diphenyl-1,4-dithiin disulphone

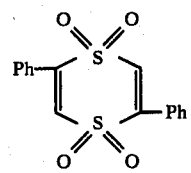

It has been observed surprisingly that by using the process of the invention, increased yields of phenols may be obtained by decomposing secondary aromatic organic hydroperoxides than when conventional acid catalysts are used. Thus, for example, yields in excess of 80 wt % of phenol have been obtained by decomposing ethylbenzene hydroperoxide in accordance with the process of the invention. Furthermore, when aromatic organic hydroperoxides in general are decomposed in accordance with the invention, significantly lower quantities of high molecular weight by-products are formed than when conventional acid catalysts are used.

The aromatic organic hydroperoxide starting material employed in the process of the present invention may contain a single alkyl-hydroperoxide group, preferably an alkyl-hydroperoxide group containing from 2 to 24, more preferably 2 to 16 and especially 2 to 12, carbon atoms. An example of such a hydroperoxide is ethyl benzene hydroperoxide. Furthermore, the alkyl-hydroperoxide group may be the sole substituent on the aromatic nucleus of the starting material or alternatively the aromatic nucleus may bear one or more other substituents, e.g. substituents selected from halogen atoms and alkyl, alkoxy and nitro groups. Decomposition of such hydroperoxides produces a correspondingly substituted phenol. In yet another alternative a dialkylaryl dihydroperoxide may be used, i.e. a compound having an aryl nucleus substituted by two alkyl-hydroperoxide groups, in which case a dihydric phenol will result from the decomposition. Such hydroperoxides may likewise bear one or more substituents thus enabling correspondingly substituted dihydric phenols to be obtained.

The decomposition of the hydroperoxide in the presence of the catalyst proceeds very readily and may be carried out under a wide variety of reaction conditions. Preferably the reaction temperature is not permitted to reach too high a level since this could lead to the thermally initiated decomposition of the hydroperoxide, producing undesirable by-products, and in an extreme case might lead to decomposition becoming too rapid and uncontrollable, and potentially explosive. A reaction temperature of from ambient to 180° C is preferred, more preferably 80° C to 150° C and especially 100° C to 140° C. The decomposition of the hydroperoxide may be sufficiently exothermic to make it desirable to control the reaction temperature in order to maintain it at the desired level. Conventional techniques can be used for this purpose, such as external cooling and/or regulating the rate at which the hydroperoxide is brought into contact with the catalyst.

Preferably the aldehyde co-product of the decomposition is continuously removed during the decomposition reaction in order to reduce the possibility of unwanted side reactions between the aldehyde and other components of the decomposition product. Thus, for example, the aldehyde may be distilled off and collected in a condenser. Removal of the aldehyde may be assisted by conducting the decomposition under reduced pressure, but generally the pressure at which the decomposition is carried out is not narrowly critical and conveniently atmospheric pressure may be used, particularly in the case where the co-product aldehyde is sufficiently volatile at the reaction temperature to be distilled off at atmospheric pressure.

The time required for completion of the reaction will depend, inter alia, on the reaction temperature but even at very low reaction temperatures is normally not more than 3 or 4 hours. At preferred reaction temperatures the decomposition will in most cases be completed within, e.g. 5 to 50 minutes at 150° C or within 1½ to 2 hours, usually not more than 1 hour, at 80° C to 120° C.

In order to moderate the decomposition, the process of the present invention is generally carried out in the presence of an inert solvent, i.e. a solvent which does not react with the hydroperoxide or its decomposition products. Thus in the case of a hydroperoxide which is solid at the reaction temperature it is preferred to dissolve the hydroperoxide in an inert solvent. The inert solvent can also be used if desired even when the hydroperoxide is liquid at the reaction temperature used. If used the inert solvent is preferably present in an amount such as to provide a solution containing from 1 to 50%, more preferably 5 to 25%, by weight of the hydroperoxide. Examples of inert solvents include benzene, toluene, xylene, ethylbenzene, chlorobenzene and nitrobenzene.

Very small quantities of the catalyst, for example a mole ratio of catalyst to hydroperoxide as low as 1:50,000 may be successfully employed in the process of the present invention. Larger quantities can also be used. However, this is unnecessary and wasteful and in some cases larger quantities of catalyst may be detrimental. In a preferred embodiment of the invention the ratio of catalyst to hydroperoxide is from 1:10,000 to 1:1000, preferably 1:5,000 to 1:1,000.

The hydroperoxides used in the process of the present invention may be prepared by the usual methods, such as autoxidation of an alkyl aryl compound. The alkyl aryl starting materials for the autoxidation may also be prepared by the usual methods such as alkylation of aryl compounds with an olefin.

The phenol and the aldehyde produced in accordance with the process of the invention may be recovered by conventional methods, for example by fractional distillation and in general the purification techniques used in the conventional acid-catalyzed process may be employed, although of course the process steps concerned with the removal of the catalyst may be omitted.

The invention will now be illustrated by the following Examples:

EXAMPLE 1

A mixture of 3009.2 parts of ethylbenzene hydroperoxide (91% w/w purity) and 6.09 parts of tetraphenyldithiin was heated at 120° C in 21,500 parts of ethylbenzene for 30 minutes in a sealed glass pressure vessel.

The resulting solution was cooled and examined quantitatively by gas chromatography using dibenzyl as an internal standard.

Phenol was formed at a molar selectivity of 82.4% with 100% conversion of the hydroperoxide.

EXAMPLE 2

A mixture of 3004.1 parts of ethylbenzene hydroperoxide (97% w/w purity) and 3.0 parts of tetraphenyldithiin was heated at 120° C in 21,500 parts of ethylbenzene for 30 minutes in an open reaction vessel (molar ratio of EBHP:catalyst = 3000:1).

The following results were obtained on analysis of the product:

Percentage conversion of EBHP — 98.3%
Molar selectivity to phenol — 69%

EXAMPLE 3

The procedure of Example 2 was repeated using 3004.8 parts of 97% w/w ethylbenzene hydroperoxide annd 6.0 parts of tetraphenyldithiin (molar ratio of EBHP:catalyst = 1500:1).

The following results were obtained on analysis of the product:

Percentage Conversion of EBHP — 100%
Molar selectivity to phenol — 81%

EXAMPLE 4

The procedure of Example 1 was repeated using various proportions of catalyst and different concentrations of ethylbenzene hydroperoxide. The results are reported in the following Table 1 from which it can be seen that conversions in excess of 95% and selectivities to phenol in excess of 75% were consistently obtained.

TABLE 1

| Ethylbenzene Hydroperoxide (Parts) 97% W/W | Type of EBHP* | EBHP % | Tetraphenyl Dithiin (parts) | Ethylbenzene Parts | Molar Ratio EBHP Catalyst | Temp (° C) | % Conversion | Molar Selectivity to Phenol |
|---|---|---|---|---|---|---|---|---|
| 1208.6 | S | 12 | 2 | 7674 | 2000:1 | 120 | 98.6 | 79.6 |
| 1208.6 | S | 12 | 4 | 7674 | 1000:1 | 120 | 100 | 82.2 |
| 604.3 | S | 6 | 1 | 8196.4 | 2000:1 | 120 | 98.2 | 78.5 |
| 604.3 | S | 6 | 2 | 8196.4 | 1000:1 | 120 | 100 | 79.9 |
| 1208.6 | S | 12 | 2 | 767.4 | 2000:1 | 130 | 99.2 | 85.6 |
| 1208.6 | S | 12 | 4 | 7674 | 1000:1 | 130 | 100 | 84.5 |
| 604.3 | S | 6 | 1 | 8196.4 | 2000:1 | 130 | 99.6 | 84.5 |
| 604.3 | S | 6 | 2 | 8196.4 | 1000:1 | 130 | 100 | 88.0 |
| 1208.6 | S | 12 | 1.32 | 7674 | 3000:1 | 130 | 100* | 76.0 |
| 584.6 | A | 5.8 | 4 | 8250 | 1000:1 | 130 | 95.2 | 87.4 |
| 584.6 | A | 5.8 | 4 | 8250 | 1000:1 | 130 | 96.6 | 85.3 |
| 584.6 | A | 5.8 | 2 | 8250 | 2000:1 | 130 | 97.2 | 84.6 |
| 584.6 | A | 5.8 | 4 | 8250 | 1000:1 | 130 | 100* | 85.5 |
| 584.6 | A | 5.8 | 1.32 | 8250 | 3000:1 | 130 | 100* | 79.4 |

*S = Synthetic (prepared by reaction between 1-phenyl ethanol and hydroperoxide)
A = Produced by autoxidation of ethylbenzene

EXAMPLE 5

The procedure of Example 1 was repeated using different compounds as catalyst. In each case the following reaction parameters were used:

| | |
|---|---|
| Reaction Temperature | 120° C |
| Reaction Time | 30 minutes |
| Hydroperoxide:Catalyst ratio | 3000:1 |
| Hydroperoxide concentration | 12% w/v |

The results are shown in the following Table 2

TABLE 2

| Catalyst | Selectivity | Conversion |
|---|---|---|
| 2,5-diphenyl-1,4-dithiin | 80% | 100% |
| 2,5-di-t-butyl-1,4-dithiin | 68.5% | 99.2% |
| 2,5-dioctyl-1,4-dithiane | 37% | 60% |
| 2,5-diphenyl-1,4-dithiin disulphone | 73 | 87% |

In the above Examples, only very small quantities of higher boiling by-products, e.g. aralkyl-substituted phenols were detected in the decomposition product.

We claim:

1. In a process comprising decomposing an aralkyl hydroperoxide, in which the aryl nucleus is substituted by at least one alkylhydroperoxide group containing from 2 to 24 carbon atoms and said aryl nucleus may be further substituted by one or more substituents selected from halogen atoms and alkyl, alkoxy and nitro groups, to produce a correspondingly substituted or unsubstituted mono- or polyhydric phenol, the improvement comprising:

effecting the decomposition at a temperature of from ambient temperature to 180° C in the presence of a catalyst comprising a compound of the formula

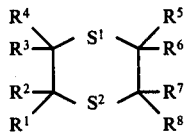

wherein $R_1$, $R_4$, $R_5$ and $R_8$ each independently represents a hydrogen atom or an unsubstituted hydrocarbyl group containing up to 24 carbon atoms, $R_2$ and $R_3$ each independently represents a hydrogen atom, an unsubstituted hydrocarbyl group containing up to 24 carbon atoms, or together represent an additional bond linking the carbon atoms to which they are attached, $R_6$ and $R_7$ each independently represents a hydrogen atom, an unsubstituted hydrocarbyl group containing up to 24 carbon atoms, or together represent an additional bond linking the carbon atoms to which they are attached, and $S_1$ and $S_2$ each independently represents a sulphur atom or a sulphoxide or sulphone group.

2. A process according to claim 1 in which the catalyst has the formula

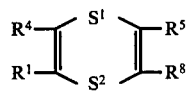

3. A process according to claim 1 in which $R^2$, $R^3$, $R^7$ and $R^8$ represent hydrogen atoms.

4. A process according to claim 1 in which $R^4$ and $R^8$ represent hydrogen atoms.

5. A process according to claim 1 in which the hydrocarbyl groups represented by any of $R^1$ to $R^8$ are alkyl groups containing from 1 to 8 carbon atoms.

6. A process according to claim 1 in which the hydrocarbyl groups represented by any of $R^1$ to $R^8$ are aryl or aralkyl groups containing from 6 to 14 carbon atoms.

7. A process according to claim 1 in which the catalyst comprises a compound of the formula

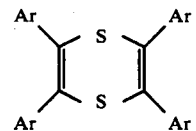

wherein each Ar represents an aryl group.

8. A process according to claim 7 in which the catalyst comprises tetraphenyl-1,4-dithiin.

9. A process according to claim 1 in which the aromatic hydroperoxide is a secondary hydroperoxide.

10. A process according to claim 1 in which the aromatic hydroperoxide is an aryl mono-alkyl hydroperoxide containing 2 to 24 carbon atoms in the alkyl moiety.

11. A process according to claim 10 in which the mono-alkyl hydroperoxide contains from 2 to 12 carbon atoms in the alkyl moiety.

12. A process according to claim 11 in which the aromatic hydroperoxide is ethylbenzene hydroperoxide.

13. A process according to claim 1 in which the decomposition is carried out in the presence of an inert solvent.

14. A process according to claim 1 in which the ratio of catalyst to hydroperoxide is from 1:10,000 to 1:1000.

15. A process according to claim 14 in which the ratio of catalyst to hydroperoxide is from 1:5000 to 1:1000.

16. A process in accordance with claim 1 wherein said aralkyl hydroperoxide is an alkylbenzene hydroperoxide in which the benzene nucleus is substituted by at least one alkylhydroperoxide group containing from 2 to 24 carbon atoms as well as zero or more other substituents selected from halogen atoms and alkyl, alkoxy and nitro groups.

17. A process in accordance with claim 1 wherein said aralkyl hydroperoxide is an aralkyl hydroperoxide in which the aryl nucleus is substituted by only one or two alkylhydroperoxide groups, each containing from 2 to 24 carbon atoms, as well as zero or more other substituents selected from halogen atoms and alkyl, alkoxy and nitro groups, and wherein a correspondingly substituted or unsubstituted mono- or dihydric phenol is produced.

18. A process in accordance with claim 16 wherein said alkylbenzene hydroperoxide is an alkylbenzene hydroperoxide in which the benzene nucleus is substituted by one or two alkylhydroperoxide groups, each containing from 2 to 24 carbon atoms as well as zero or more other substituents selected from halogen atoms and alkyl, alkoxy and nitro groups, and wherein a correspondingly substituted or unsubstituted mono- or dihydric phenol is produced.

19. A process in accordance with claim 1 wherein said aralkyl hydroperoxide is an alkylbenzene hydroperoxide in which the benzene nucleus is substituted by at least one alkylhydroperoxide group containing 2 to 24 carbon atoms, and is otherwise unsubstituted.

20. A process in accordance with claim 19 wherein said alkylbenzene hydroperoxide is one in which the benzene nucleus is substituted by only one or two of said alkylhydroperoxide groups.

21. A process in accordance with claim 20 wherein said alkylbenzene hydroperoxide is one in which the benzene nucleus is substituted by only one of said alkylhydroperoxide groups and wherein unsubstituted monohydric phenol is produced.

* * * * *